(12) United States Patent
Seguin

(10) Patent No.: US 8,492,417 B2
(45) Date of Patent: Jul. 23, 2013

(54) TOPICAL USE OF THIAZOLIDINE DERIVATIVES AGAINST CONSEQUENCES OF OXIDATIVE STRESS OF SKIN

(71) Applicant: Exsymol S.A.M., Monaco (MC)

(72) Inventor: Marie Christine Seguin, Monaco (MC)

(73) Assignee: Exsymol S.A.M. (MC)

( * ) Notice: Subject to any disclaimer, the term of this patent is extended or adjusted under 35 U.S.C. 154(b) by 0 days.

(21) Appl. No.: 13/708,462

(22) Filed: Dec. 7, 2012

(65) Prior Publication Data

US 2013/0095052 A1 Apr. 18, 2013

Related U.S. Application Data

(62) Division of application No. 12/233,661, filed on Sep. 19, 2008.

(30) Foreign Application Priority Data

Sep. 21, 2007 (FR) ...................... 07 06641

(51) Int. Cl.
*A61K 31/425* (2006.01)
*A61K 9/00* (2006.01)
*A61K 8/02* (2006.01)

(52) U.S. Cl.
USPC ............................ 514/369; 424/400; 424/401

(58) Field of Classification Search
USPC .................................. 514/369; 424/400, 401
See application file for complete search history.

(56) References Cited

U.S. PATENT DOCUMENTS 6,004,543 A * 12/1999 Galey .............................. 424/62
7,109,223 B2 * 9/2006 Han et al. ...................... 514/369

\* cited by examiner

*Primary Examiner* — Abigail Fisher
(74) *Attorney, Agent, or Firm* — Volpe and Koenig, P.C.

(57) ABSTRACT

The invention concerns a cosmetic care method for opposing destructive effects of oxidative stress and its toxic by-products, comprising administering topically to a patient in need thereof, a derivative of formula (I):

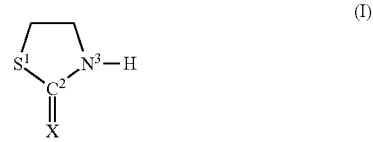

in which X is oxygen or sulphur.
The invention especially applies to the domain of skin protection and more especially against cutaneous consequences of oxidative stress.

17 Claims, No Drawings

TOPICAL USE OF THIAZOLIDINE DERIVATIVES AGAINST CONSEQUENCES OF OXIDATIVE STRESS OF SKIN

This application is a Divisional of U.S. application Ser. No. 12/233,661, which was filed Sep. 19, 2008 and claims priority under 35 U.S.C. 119 to French application No. FR07/06641 filed Sep. 21, 2007, which are incorporated by reference herein as if fully set forth.

The invention concerns the cosmetic use of thiazolidine derivatives, particularly in the domain of skin protection and more especially in the struggle against oxidative stress and its cutaneous consequences.

By its role as an external envelope of the body against the atmosphere, skin is an organ particularly sensitive to the environment to which it is submitted. This can be of a pro-oxidant nature, due to prolonged exposure to the sun's ultraviolet rays, smoky atmospheres or those containing atmospheric chemical pollutants. These aggressions of an exogenous nature generate an excess of very reactive species, radical or not, with a strong oxidant potential. These are notably species derived from molecular oxygen, which are often named reactive oxygen species or ROS, like the superoxide anion $O_2^{\circ-}$, the hydrogen peroxide $H_2O_2$, the oxygen singulet $^1O_2$, the hydroxyl radical $OH^\circ$.

This overproduction of ROS is then responsible for biological constituent alterations of skin, in particular of those met in the cutaneous cells (DNA, proteins, lipids, glucides). The formation of by-products issued from degradation of these biological molecules, and in particular of those issued from the peroxidised membrane phospholipids by the ROS, is also harmful to skin. Finally, exposure of a skin to an overproduction of ROS also initiates complex biochemical reactions, which are at the origin of pro-inflammatory cytokine production, mutagen metabolites, and the death of cutaneous cells (Briganti S. and al., J. Eur. Acad. Dermatol. Venereol. (2003), vol. 17, pp. 663-669).

In general, all these phenomena are harmful to skin, more particularly when they reach the deep layers, notably in the dermis. It is also well established today that a loss of control by the skin caused by the excessive presence of ROS, leading to a state commonly designated as "oxidative stress", is clearly involved in the start of numerous cutaneous disorders or anomalies: induced ageing, immunosuppression, inflammation/erythema, carcinogenesis, irritation, etc (Bickers D. R. and al., J. Invest. Dermatol. (2006), vol. 126, pp. 2565-2575 and quoted references).

Physiologically, and despite the existence of natural antioxidant systems of regulation and protection, enzymatic (superoxide dismutase, catalase, peroxidase, etc) or non-enzymatic (vitamins A, C, D or E, carotenoids, glutathione, trace elements, etc), the skin displays a quick depletion of defence, when confronted with an important flux of free radicals or ROS.

For many years, the conception of systems capable of limiting the deleterious effects of this reactive species overproduction, or even to capture or to trap them, has become a major research topic. Thus in order to palliate the skin's physiological insufficiencies, numerous natural or synthetic molecules (plant or animal extracts) have been developed and proposed as antioxidant or antiradical supplements administered orally or by topical application (Darwin M. and al., Skin Pharmacol. Physiol. (2006), vol. 19, pp. 238-247).

However, according to the invention, an efficient protection against these so-called first generation ROS is shown for a number of antioxidant or antiradical molecules belonging to the state of the technique. By "first generation ROS", it is to necessary to understand the species derived from molecular oxygen reduction ($O_2^{\circ-}$, $H_2O_2$, $^1O_2$, $OH^\circ$, $ONOO^-$, etc). On the other hand, an action regarding the oxidation by-products or so-called second generation products (toxic aldehydes, final products issued from the lipid peroxidation, etc) which are also toxic and result in chain reactions of primary species with the biochemical components of the cell is more rarely justified.

In general, it remains that the selection of an antioxidant substance said to be "efficient", notably for human administration, is difficult. It is also to note that it is often considered an in vitro benefit, which is seldom confirmed clearly in vivo (Bickers D. R. and al., J. Invest. Dermatol. (2006), vol. 126, pp. 2565-2575).

Indeed, in addition to the multi-layered structural complexity of human skin and in consequence to an oxidative stress expressing itself differently, the previously mentioned antioxidant substance must combine:

an efficiency towards the largest possible panel of reactive oxygen species, and in consequence possess a broad spectra of "anti-stress" properties, an efficiency towards toxic by-products of oxidative stress, a reactivity in contact with ROS such as it does not lead to toxic rearrangement product formation, a favourable cutaneous penetration (and thus a bioavailability) in order to reach different cutaneous tissue sites, finally, a resistance to hydrolytic skin systems (and thus a resistance to its metabolization), which is a guarantee of its in situ activity.

The present invention has been developed in this context to satisfy this request for products or preparations able to oppose the destructive effects of oxidative stress and its toxic by-products as efficiently as possible, notably in the deep skin layers.

Thus, the applicant's choice falls on thiazolidine heterocyclic derivatives, in particular on 2-oxo-1,3-thiazolidine. Reasons for this selection are multiple:

In the first place, the structure and properties displayed by the 2-oxo-1,3-thiazolidine compound constituted an advantageous response to different previous cited criteria, which is illustrated by:

a favourable cutaneous penetration revealed by obtaining a partition coefficient logarithmic value ("Log P") comparable to the one for known trans-stratum corneum permeant compounds (Arct J. and al., SOFW-J. (2003), vol. 129, pp. 2-9) [test 1 below], a note-worthy antioxidant activity with regard to its capacity to react on a large panel of ROS molecules [with $O_2^\circ$, $H_2O_2$, et $OH^\circ$ produced thanks to oxidase/hypoxanthine xanthine oxidant pair) [test 2 below], an unsuspected ability to neutralize highly toxic electrophile species issued from lipid peroxidation, from 4-hydroxynonenal or "4-HNE" aldehyde [tests 3 and 4 below].

In second place, and it is another important aspect of the invention, while following the 2-oxo-1,3-thiazolidine heterocycle in oxidant aqueous medium with ROS, especially hydrogen peroxide (one of the most toxic ROS for living tissue), the applicant unexpectedly discovered with regard to an almost-quantitative evolution and the absence of oxidized intermediate forms, that this heterocycle easily generated the stable and ultimate oxidation product, taurine, from once the heterocycle is placed under oxidative conditions [test 5 below]. Such behaviour is very useful because it guarantees a total absence of toxicity of 2-oxo-1,3-thiazolidine reaction by-products with $H_2O_2$. Taurine is actually an amino acid naturally present in skin. In addition, the cutaneous interest to form taurine is even today reinforced, since it is recently considered as an essential osmolyte in "UV-induced" stress submitted keratinocytes homeostasis (Jancke G. and al., J. Invest. Dermatol. (2003), vol. 121, pp. 354-361).

The 2-oxo-1,3-thiazolidine compound, as such, is not a new product. In the state of the technique, it is to raise its synthesis from aminoethanethiol and diphenyl carbonates according to a process and particular conditions which usually grant a phosgene-type chemical reactivity to various cyclic polycarbonates issued from plastic retreatment (Hata S. and al., J. Appl. Polym. Sci. (2003), vol. 90, pp. 2959-2968). On the other hand and with regard to the previous art brought to the applicant's attention, no cosmetic or dermatologic application is known for specifically this "2-oxo" sulphured-heterocycle, nor one or several properties regarding oxidative stress for its "thiono" analog in position 2 for which, the applicant also observed the taurine formation in oxidative conditions [see test 5 below].

It is nevertheless to signal the 2-oxothiazolidine-4-carboxylic acid existence. This compound, as an ester or amide derivative, is on the other hand the object of various and numerous interests in cosmetics and dermatology: photoprotection (FR 2 877 004 and FR 2 854 160 patents), combating hair loss (EP 0 656 201 patent), depigmentation agents (U.S. Pat. Nos. 6,063,389 and 6,007,827 patents) or desquamate agents (FR 2 816 838 patent), etc. Reading the literature concerning the protection of skin in a general manner, there is only a cutaneous benefit thanks to an action of stimulation of cell natural defences, particularly of a stimulating action on glutathione intracellular synthesis. Furthermore this compound is not a precursor of taurine. At last, this compound is structurally different from 2-oxo-1,3-thiazolidine, so that this work does not foretell the effects of 2-oxo-1,3-thiazolidine.

Thus, according to the first aspect, and with this "anti-stress" pluri-functional dimension represented by the 2-oxo-1,3-thiazolidine compound behaviour in a pro-oxidant environment such as skin submitted to an oxidative stress, the invention has for object the use of a derivative of general formula (I) as active ingredient in a cosmetic composition:

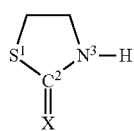

in which X represents an atom of oxygen or sulphur, the said derivative or the said composition being intended for skin protection against any stress generating free radicals or reactive oxygen species.

The preferred compound of above formula (I) is such that X represents an atom of oxygen.

The above-mentioned use is preferentially maintained against a stress with an origin chosen among atmospheric pollution, contact with chemical xenobiotics or smoky atmospheres, and more specifically ultraviolet radiation. The present invention aims to forestall and to fight against cutaneous signs resulting from such stress, notably against varied events connected to skin ageing. It especially applies to the domain of sun protection, with regard to:

the proved involvement today of 4-hydroxynonenal or "4-HNE" in UV-A submitted cell apoptosis (Yang Y. and al., J. Biol. Chem. (2003), vol. 278, pp. 41380-41388), combined to the strong efficiency of the above mentioned 2-oxo-1,3-thiazolidine compound to trap this toxic aldehyde the reported existence of an "UVA-induced" stress in the skin dermis and harmful to the protein constituents of the extra-cellular matrix (Wondrak G. T. andal., J. Invest. Dermatol. (2003), vol. 121, pp. 578-586), combined with the topical availability of the same 2-oxo-1, 3-thiazolidine compound in these same dermal layers, and in addition to its intrinsic features: absence of chemical ionisable functions to skin physiological pH, non-sensitivity to skin hydrolases, weak molecular weight the experimental assessment recently lead by the applicant in the efficiency of the 2-oxo-1,3-thiazolidine compound towards a "UVA-induced" stress ([test 6] below)

According to the second aspect, the present invention also spreads to a cosmetic composition comprising, in association with any physiologically compatible excipient with skin, and as main active ingredient, the derivative of formula (I) such as defined previously, the said composition being intended for protecting skin against any stress generating free radicals or reactive oxygen species.

More precisely, the said composition is intended for protecting skin against a "UV-induced" stress, and the derivative of general formula (I) is such that X represents an atom of oxygen.

Advantageously, the quantity of the said derivative of formula (I) in the above-mentioned composition comprises between 0.01 and 10% in weight in relation to total weight of the composition, preferably between 0.05 and 5% in weight, even better between 0.5 and 5% in weight.

An example of a physiologically compatible excipient with skin that one can mention, is a surfactant, a preservative, body fat, a colorant, an emulsifier, a gelling agent, an emollient, a moisturizer, a pigment, or all other adjuvants usually used in cosmetics.

According to an embodiment of the invention and in order to reinforce the antioxidant or antiradical activity, the said composition is susceptible to comprise, furthermore, another active element chosen among antioxidant, antiradical and/or anti-pollution agents found on the market, in such a way that the intrinsically attached effect to the compositions according to the invention is not altered by the considered addition. These antioxidant, antiradical or anti-pollution agents commonly found on the market can be:

vitamins such as vitamins C E, and D, enzymes such as superoxide dismutases, catalases, and peroxidases, with synthetic, plant, animal, bacterial or recombinant origin for example, the phenolic compounds such as polyphenols (epigallocatechin-3-gallate) and notably ferulic acid, silymarin, genistein, apigenin, resveratrol flavonoids.

Still in an optional way, the above-mentioned composition can also associate a UV-A or B sunscreen, or their mixture, of organic (benzophenone derivatives) or inorganic (metallic oxides) nature, or even a cosmetic active ingredient with a secondary effect, such as a moisturizing agent, a smoothing agent, a pigmenting agent, an agent stimulating the synthesis of epidermic and dermic macromolecules, and this, whilst maintaining that the said cosmetic active ingredient and its quantity are present in a way that properties of the composition according to the invention are not altered by the considered addition.

The compositions according to the invention are adapted to a topical cutaneous administration and presented under all typical forms used for such an administration. In a preferred embodiment of the invention, they are formulated under the form for instance of emulsions, creams, milks, gels, lotions, etc.

As an illustration, it is mentioned hereafter some examples of cosmetic composition formulation according to the invention, containing the aforementioned 2-oxo-1,3-thiazolidine or 2-thiono-1,3-thiazolidine heterocycles:

| Formula A (cream) | |
|---|---|
| 2-oxo-1,3-thiazolidine | 1% |
| Hydrogenated polyisobutene | 7% |
| Isobutyl myristate | 3% |
| Cetyl Palmitate | 7% |
| Ethylene glycol monostearate | 5% |
| Sorbitan laurate | 2% |
| Polysorbate 20 | 2% |
| Carbomer (acrylate copolymer/ acrylamide & mineral oil) | 0.3% |
| Phenoxyethanol | 0.5% |
| Water qsp | 100% |

| Formula B (gel) | |
|---|---|
| 2-thiono-1,3-thiazolidine | 0.5% |
| Carbomer (acrylate copolymer/ acrylamide & mineral oil) | 0.3% |
| Sodium benzoate | 0.2% |
| Sorbic acid | 1% |
| 1,3-butanediol | 10% |
| Glycerine | 5% |
| Sodium carbonate | 0.13% |
| Phenoxyethanol | 0.9% |
| Water qsp | 100% |

Finally, according to a last aspect, the present invention concerns a cosmetic treatment process aiming to fight against the oxidative stress of skin and its consequences. The process is used by applying the previously defined compositions, preferentially with a composition comprising the 2-oxo-1,3-thiazolidine derivative.

Preferably and in order to reinforce the said process, this latter can also be used with concomitance to oral supplementation of an antioxidant substance typically found on the market, for instance such as listed here-above. To this end, the said process can comprise also of the oral administration of an antioxidant substance to the individual person for which the cosmetic treatment is intended. The administration on the skin of a composition according to the invention and the oral administration of an antioxidant substance take place preferably at the same time.

As purely an indication, the invention is hereafter illustrated, by the following tests described above for the invention (tests 1 to 6). It is also to signal that the first results of an in vivo study on man can illustrate the use of thiazolidine derivatives according to the present invention.

Test 1: Partition Coefficient of the 2-oxo-1,3-thiazolidine Compound

The values of n-octanol/water (Log P) partition coefficient have been experimentally obtained in accordance with the protocol described in the OECD guidelines n° 107 (adopted the 27 Jul. 1995) for tests on chemicals.

The log P of the 2-oxo-1,3-thiazolidine compound according to the invention is compared to the one obtained for caffeine and ethanol (table 1 below).

TABLE 1

| Compound | Log P |
|---|---|
| ethanol | −0.31 |
| caffeine | −0.07 |
| 2-oxo-1,3-thiazolidine | −0.27 |

The 2-oxo-1,3-thiazolidine result is comparable to the one obtained for the known trans-stratum corneum permeant compound.

Test 2: Demonstration of the Antioxidant Effect of the 2-oxo-1,3-thiazolidine Compound a) Measure the Scavenging Activity of the Hydroxyl Radical (OH°)

The method, described by Rehman A. and coll. (British J. Pharmacol. (1997), vol. 122, pp. 1702-1706), is used for the determination of the scavenging speed constant of the hydroxyl radical [Ks (OH°)], the compound 2-oxo-1,3-thiazolidine according to the invention being compared to a molecule of reference, taurine.

Experimentally, the tested substance is dissolved in a buffered medium of pH 7,4 to which is added a generating medium of OH°. Following one hour of incubation at 37° C., the reaction is stopped with the help of trichloroacetic acid. After addition of a colorimetric revealer, thiobarbituric acid, the absorbance is measured at 532 nm for different concentrations, then the relative Ks (OH°) is calculated for each of the substances. The results are reported below in table 2a.

TABLE 2a

| Compound | Ks (OH°) (109.M-1.s−1) |
|---|---|
| taurine | 5.32 |
| 2-oxo-1,3-thiazolidine | 13.52 |

The results, taking the middle values obtained from five independent experiments underline an extensively superior capacity to trap the hydroxyl radical (OH°) for the 2-oxo-1,3-thiazolidine compound compared to taurine, superior even to ascorbic acid (vitamin C) for which the literature reports a Ks) (OH°) of 10.1 Gigas.M-1.s-1 (Cabelli D. E., J. Phys. Chem. (1983), vol. 87, pp. 1809-1812).

b) Measure of the "Global" Antioxidant Power

The production system of ROS, described by Nowak D. and coll. (Biomed. Biochem. Acta (1991), vol. 50, pp. 265-272) and involving the oxidase/hypoxanthine xanthine pair, is used for the determination of the "global" antioxidant power. This is characterized by the sum of the effects against the superoxide anion $O_2^{°-}$, hydrogen peroxide $H_2O_2$, and the hydroxyl radical OH°, and is expressed by following the percentage of protection of a "detecting" molecule, desoxyribose.

The 2-oxo-1,3-thiazolidine compound according to the invention is also compared to taurine. Experimentally, the tested substance is dissolved in a buffered medium at pH 7.5, supplemented with NaCl, $MgCl_2$ et $CaCl_2$. After their incubation at 37° C. in the presence of the oxidase/hypoxanthine xanthine pair, EDTA and desoxyribose, the reaction is stopped with the help of trichloroacetic acid. After addition of thiobarbituric acid, an optic density measure at 532 nm is carried out, expressed later as percentage of desoxyribose protection (following comparison with a control). Results are reported in the hereafter table 2b:

TABLE 2b

| Compound | % protection |
|---|---|
| taurine (20 mM) | 19 |
| 2-oxo-1,3-thiazolidine (10 mM) | 19 |
| 2-oxo-1,3-thiazolidine (20 mM) | 25 |

For the 2-oxo-1,3-thiazolidine compound, a desoxyribose protection superior to the one with taurine is observed (identical protection for a concentration two times less).

Test 3: Demonstration of the Capacity of the 2-oxo-1,3-thiazolidine Compound to Neutralize 4-hydroxynonenal Cytotoxicity The experimental study has been carried out on a fibroblastic line of hamster called V79, maintained in humid atmosphere at 37° C. and 5% $CO_2$, then seeded in 96 wells plates at the rate of $0.5.10^4$ cells per well. The cells are then submitted to a state of toxic stress, with replacement of the culture medium by a medium containing 4-hydroxynonenal (or 4-HNE) at 6 ppm concentration, medium to which is simultaneously added the 2-oxo-1,3-thiazolidine compound according to the invention.

The cellular viability of fibroblasts is measured by the incorporation method to the bromide of 3-(4,5-dimethylthiazol-2-yl)-2,5-diphenyltetrazolium (or MTT). The results, taking the middle values obtained from three independent experiments, are presented below in table 3, in comparison with those for the N-acetyl-cysteine at 2 mM chosen as a positive reference molecule (total restoration of cellular viability in relation to a control and the non stressed cells with 4-HNE).

TABLE 3

| | % cellular viability |
|---|---|
| control | 100 |
| HNE 6 ppm | 34 |
| N-acetyl-cysteine 2 mM | 126 |
| 2-oxo-1,3-thiazolidine 0.1 mM | 40 |
| 2-oxo-1,3-thiazolidine 1 mM | 58 |
| 2-oxo-1,3-thiazolidine 2.5 mM | 100 |

According to the invention, the results of table 3 underline, for the 2-oxo-1,3-thiazolidine compound, a dose-dependent cellular viability, along with an identical capacity as the reference to protect cells submitted to a 4-HNE-stress.

Test 4: Demonstration of the Anti-clastogen Effect of the 2-oxo-1,3-thiazolidine Compound in Presence of a Genotoxic Concentration of 4-hydroxynonenal.

The study has been carried out according to identical experimental conditions (sowing) to those presented in the here-above test 3, with cell exposure to a state of "4-HNE stress" at ppm genotoxic concentration, as described (Eckel P. M., Molecular Aspects of Medicine (2003), vol. 24, pp. 161-165) as generating cellular DNA breaks and micronucleus formation (clastogen effect).

The micronucleus cell number is counted following reading of the slides with epifluorescence microscope, on 2000 cells and after marking with orange acridine (DNA colorant).

Results, taking the middle values obtained from two independent experiments, are presented below in table 4, in comparison with those for N-acetyl-cysteine at 2 mM chosen as a positive reference molecule (number of micronucleus cells close to the non-exposed control).

TABLE 4

| | Cell number with micronucleus/2000 cells |
|---|---|
| control | 19 |
| stress-HNE 1 ppm | 58 |
| N-acetyl-cysteine 2 mM | 27 |
| 2-oxo-1,3-thiazolidine 5 mM | 21 |

It is observed thus a capacity to prevent micronucleus cell formation induced by a 4-HNE genotoxic stress.

Test 5: "in tubo" Demonstration of Taurine Formation When in Contact with a $H_2O_2$ Solution.

To a 10% aqueous solution of 2-oxo-1,3-thiazolidine or 2-thiono-1,3-thiazolidine derivatives according to the invention, buffered at pH 7.4 and 37° C., 4 equivalents of a solution of hydrogen peroxide $H_2O_2$ are added, therefore a weak excess of oxidant species compared to the 3 theoretical equivalents necessary for a complete conversion (100%) in taurine. The evolution of medium reaction is followed by liquid chromatography (HPLC equipped with UV detector at 254 nm), leading to the results shown below in table 5 and to the demonstration of an almost-exclusive and quantitative formation of taurine after reaction of the 2-oxo-1,3-thiazolidine or 2-thiono-1,3-thiazolidine derivatives in contact with $H_2O_2$.

TABLE 5

| | taurine (% formation from 2-oxo-1,3-thiazolidine) | taurine (% formation from 2-thiono-1,3-thiazolidine) |
|---|---|---|
| 3 h | 38 | 30 |
| 7 h | 56 | 50 |
| 24 h | 82 | 77 |
| 48 h | 93 | 89 |

Test 6: Demonstration of the Protector Effect of the 2-oxo-1,3-thiazolidine in Presence of a "UVA-induced" Stress The study has been carried out according to identical experimental conditions (sowing) to those presented in the here-above tests 3 and 4, but with an exposure of V79 cells to ultraviolet radiation ($\lambda$315-400 nm) with the moderate dose of 5 J. $cm^{-2}$ ("UVA-induced" stress).

The formation of intracellular ROS is measured with the permeant fluorescent probe "CMDCF" derived from fluorescein (10 μm, 15 minutes incubation).

The percentages of CMDCF cells said "positive" (cells with intracellular formation of ROS are presented below in table 6, in comparison with unirradiated cells, then with cells treated with N-acetyl-cysteine (reference molecule) and different concentrations of 2-oxo-1,3-thiazolidine compound.

TABLE 6

| | % of CMDCF positive cells |
|---|---|
| Unirradiated cells | 3 |
| Irradiated cells | 30 |
| Irradiated cells + N-acetyl-cysteine 5 mM | 4 |
| Irradiated cells + 2-oxo-1,3-thiazolidine 0.625 mM | 24.7 |
| Irradiated cells + 2-oxo-1,3-thiazolidine 1.25 mM | 15.3 |

TABLE 6-continued

| | % of CMDCF positive cells |
|---|---|
| Irradiated cells + 2-oxo-1,3-thiazolidine 2.5 mM | 12 |
| Irradiated cells + 2-oxo-1,3-thiazolidine 5 mM | 7.3 |

The 2-oxo-1,3-thiazolidine compound according to the invention shows a dose-dependent ability to protect cells submitted to a "UVA-induced" stress, and similar to the reference molecule.

The invention claimed is:

1. A method of cosmetic care for the treatment of the destructive effects of oxidative stress and toxic by-products thereof, the method comprising topically administering to a patient in need thereof a composition including a compound having the structure of formula (I):

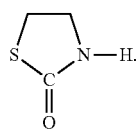

(I)

2. The method according to claim 1, wherein said compound is administered against stress generating free radicals or reactive oxygen species.

3. The method according to claim 1, wherein taurine is produced from said compound when said compound is in contact with reactive oxygen species.

4. The method according to claim 1, wherein said compound is administered for neutralizing toxic electrophile species issued from lipid peroxidation.

5. The method according to claim 1, wherein the step of administering is done in response to exposure to ultraviolet radiation, atmospheric pollution, chemical xenobiotics or smoky atmospheres.

6. The method according to claim 5, wherein the exposure is to ultraviolet radiation.

7. The method according to claim 1, wherein the step of administering topically to a patient in need thereof is to skin.

8. A method of cosmetic care for treating oxidative stress of skin generating free radicals or reactive oxygen species, the method comprising applying on the skin of a patient in need thereof a composition comprising a physiologically compatible skin excipient and a taurine precursor of formula (I):

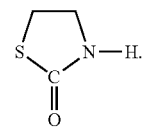

(I)

9. The method according to claim 8, wherein said taurine precursor is present between 0.01 and 10% in weight in relation to the total weight of the composition.

10. The method according to claim 8, wherein said physiologically compatible skin excipient is selected from a group consisting of a surfactant, a preservative, body fat, a colorant, an emulsifier, a gelling agent, an emollient, a moisturizer, and a pigment.

11. The method according to claim 8, wherein said composition further comprises an agent selected from the group consisting of antioxidant, antiradical and anti-pollution agents.

12. The method according to claim 8, wherein said composition further comprises one or more agent selected from the group consisting of organic UV-A sunscreen, organic UV-B sunscreen, inorganic UV-A sunscreen, inorganic UV-B sunscreen.

13. The method according to claim 8, wherein said composition is applied in the form of an emulsion, cream, milk, gel, or lotion.

14. The method according to claim 8, further comprising orally administering an antioxidant substance.

15. The method according to claim 8, wherein the step of administering is done in response to exposure to ultraviolet radiation, atmospheric pollution, or contact with chemical xenobiotics or smoky atmospheres.

16. The method according to claim 15, wherein the exposure is to ultraviolet radiation.

17. The method according to claim 4, wherein the toxic electrophilic species is 4-hydroxynonenal.

\* \* \* \* \*